(12) United States Patent
Churakov et al.

(10) Patent No.: US 11,707,195 B2
(45) Date of Patent: Jul. 25, 2023

(54) SYSTEM, METHOD, AND COMPUTER READABLE MEDIUM FOR MONITORING, TRACKING, AND TRACING TEMPERATURE AND HUMIDITY UNDER GARMENT

(71) Applicants: Dmitri Churakov, Tel Aviv-Jaffa (IL); Oleg Borisov, Korolev (RU)

(72) Inventors: Dmitri Churakov, Tel Aviv-Jaffa (IL); Oleg Borisov, Korolev (RU)

( * ) Notice: Subject to any disclaimer, the term of this patent is extended or adjusted under 35 U.S.C. 154(b) by 323 days.

(21) Appl. No.: 16/938,644

(22) Filed: Jul. 24, 2020

(65) Prior Publication Data

US 2022/0022755 A1     Jan. 27, 2022

(51) Int. Cl.
| | | |
|---|---|---|
| *A61B 5/01* | (2006.01) | |
| *G01K 1/024* | (2021.01) | |
| *A61B 5/00* | (2006.01) | |
| *A41D 13/005* | (2006.01) | |
| *G01K 13/20* | (2021.01) | |
| *A41D 27/20* | (2006.01) | |
| *G01K 1/14* | (2021.01) | |

(52) U.S. Cl.
CPC .............. *A61B 5/01* (2013.01); *A41D 13/005* (2013.01); *A61B 5/0008* (2013.01); *A61B 5/6804* (2013.01); *A61B 5/7282* (2013.01); *G01K 1/024* (2013.01); *G01K 1/14* (2013.01); *G01K 13/20* (2021.01); *A41D 27/205* (2013.01); *A61B 5/6898* (2013.01); *A61B 2562/029* (2013.01); *A61B 2562/0271* (2013.01)

(58) Field of Classification Search
CPC ....... A61B 5/01; A61B 5/0008; A61B 5/6804; A61B 5/7282; A61B 5/6898; A61B 2562/0271; A61B 2562/029; G01K 13/20; G01K 1/024; G01K 1/14; A41D 13/005; A41D 27/205

See application file for complete search history.

(56) References Cited

U.S. PATENT DOCUMENTS

| | | | |
|---|---|---|---|
| 2011/0015498 A1* | 1/2011 | Mestrovic | A61B 5/6807 600/592 |
| 2014/0018641 A1* | 1/2014 | Yoshino | A61B 5/7275 600/301 |
| 2017/0196513 A1* | 7/2017 | Longinotti-Buitoni | A61B 5/7405 |
| 2019/0313913 A1* | 10/2019 | Fu | G16H 40/67 |
| 2019/0343397 A1* | 11/2019 | Meisal | A61B 5/01 |
| 2020/0229514 A1* | 7/2020 | Cooper | H04B 1/385 |

* cited by examiner

*Primary Examiner* — Matthew Kremer
*Assistant Examiner* — Om Patel
(74) *Attorney, Agent, or Firm* — Inventa Capital PLC

(57) ABSTRACT

The invention relates to systems for temperature and humidity monitoring under garments and is characterized by that it contains at least one internal electronic module located under the garment and an external electronic module with sensors for temperature and humidity monitoring, storage devices connected to the electronic modules wirelessly (for example, via Bluetooth), and the receiving device, which provides the user with the possibility to monitor the current temperature and humidity of the observed object.

7 Claims, 6 Drawing Sheets

SYSTEM, METHOD, AND COMPUTER READABLE MEDIUM FOR MONITORING, TRACKING, AND TRACING TEMPERATURE AND HUMIDITY UNDER GARMENT

FIELD OF THE INVENTION

The present invention relates to system, method, and computer-readable medium used to screen human body temperature. More specifically, this invention is directed to an approach to noninvasively and remotely detection of a core body temperature in a warm-blooded subject, such as human or animal and systems for temperature and humidity monitoring under the garment and can be used in such items of clothing as outerwear and shoes for monitoring the state parameters of individual parts of the body under the garment.

BRIEF DESCRIPTION OF THE INVENTION

Today all countries in the world are threatened by the spread of new, deadly, and contagious diseases, such as coronavirus (COVID19), or the possibility of terrorist attacks with biological weapons. Travelers may spread dangerous microbes intentionally or unintentionally. The screening technologies that detect guns, knives, or explosives are of little value against these new biological hazards. There are numerous standard medical diagnostic techniques.

Unfortunately, these techniques are time-consuming and unsuited for mass screening at places such as airports, ports of entry, immigration stations, crowded malls, or places of business. COVID19 have involved people who have cared for a COVID19 patient or had direct contact with infectious material such as respiratory secretions. COVID19 may be acquired by a healthy individual if that individual touches the skin of an infected person or objects which are contaminated with infectious droplets and then in turn touches the eye(s), nose or mouth of the healthy individual. This can readily happen when a person, sick with COVID19, coughs or sneezes droplets onto themselves, other people or nearby surfaces. COVID19 may also be spread more broadly through the air or by other ways not yet known.

Outerwear and shoes are used to maintain comfortable temperature and humidity of the body during various forms of activity and create a barrier to human exposure to temperature and environmental precipitation. At the same time, environmental parameters affect the physical condition of each person in different ways.

Therefore, the conditions, under which the temperature and humidity of the body go beyond the critical limits, vary under the same outwear and are individual for each person, and thus it is difficult and not always possible to control the state parameters of separate body parts under garments.

Certain categories of people small children, elderly people, people with disabilities—cannot independently control the temperature and humidity values of their bodies under garments, especially when those values go beyond critical indicators, and thus such people need remote monitoring by third parties—relatives, nannies, nurses, medical workers.

It is difficult for athletes or travelers to carry out continuous monitoring of body temperature and humidity under clothing without interrupting their activities as well as under the conditions of extreme loads on their bodies and various weather conditions. In the context of a pandemic of viral diseases, medical personnel may need to simultaneously control the temperature and hydration of many people.

Failure to inform the person or medical personnel about critical values of temperature and humidity of the body or adverse values of temperature and humidity of the environment can lead to health declining, and in some cases to death threat.

Thus, monitoring of temperature and humidity values under the garment and comparing them with the values of temperature and humidity of the environment is necessary for people staying under the supervision of doctors and important for people having an active lifestyle.

Moreover, it is known that one of the basic principles of modern medicine and a healthy lifestyle is personalization and prevention. Personalization is determined by an individual approach to each person, depending on the individual characteristics of the body. Prevention is determined by an early action to prevent disease. There exists a technical solution for outerwear with a built-in dual thermometer that displays the measured temperature on the inner and outer surfaces of the clothes, giving a sound and light signal in case of elevated temperature under the outdoor wear. The disadvantages of the known technical solution are: limited possibility of remote monitoring of temperature and limitation of measurement only by one parameter of the human condition—temperature.

Other known technical solution is baby clothes with the device for determining humidity under the clothes, which consists of a clothes body, a humidity measuring sensor located on the back of the clothes, and an alarm for notification. The disadvantage of the known technical solution is a wired connection between the elements of the device and the lack of the ability to visually monitor the parameters of the child's condition.

Other known technical solution relates to school uniform and is intended for satellite positioning and monitoring of the child's condition in real time, consists of a school uniform, satellite positioning device, a device for monitoring the condition of the child, including temperature and heart rate sensors that provide wireless remote data transmission. The disadvantages of the known technical solution are the small number of monitored parameters of the state of the child and the absence of an alarm in case critical values are reached.

There is another technical solution of cold protective clothing with the device for determining the temperature and humidity of the environment, located in a convenient place on the chest and made in the form of a round sign with an indicator on the outer surface. The disadvantage of the known technical solution is the lack of built-in device functions for determining temperature and humidity under clothing.

Another known technical solution is the device for monitoring body temperature under clothing, consisting of a temperature indicator, located outside the clothing, temperature sensors, located on the body or under the clothing in places of controlled body areas, and connected to the sensors and temperature indicator of a microprocessor module that processes incoming information on temperature values and activates indicators located outside the clothes. The device is designed to automatically transmit temperature information using a cell phone by sending an SMS to one or more phones of observers.

The disadvantage of the known technical solutions is the difficulty of controlling the values and determining the parameters of the critical state of the observed object under its garment, due to: the lack of the ability to measure humidity under the clothing; inconvenient fastening of the elements of devices for measuring the state parameters of the observed object under the clothing, due to the presence of wire mounts; the lack of the ability to save measurement data of the state parameters measured under the clothing of the observed object, and measurements of the environmental parameters during the observation session.

To the extent as being effective, there is always a need for new and improved systems and methods to simplify the monitoring of critical parameters of the state of the observed object under the clothing.

The present invention aims to solve this problem by simple and convenient means.

SUMMARY OF THE INVENTION

A computer implemented system is designed to monitor individual body temperature and to manage alarms and access in areas with flows of people in transit such as hospitals, supermarkets, railway stations, schools, airports, companies, offices, shopping centers, and the like. The computer implemented system of the present invention is used for temperature and humidity monitoring under a garment of an object to be observed. The computer implemented system includes at least one internal electronic module located under the garment and at least one external electronic module, the at least one internal electronic module and the at least one external electronic module including sensors for temperature and humidity monitoring and internal storage devices wirelessly connected to the at least one internal electronic module and the at least one external electronic module.

The computer implemented system also includes a receiving device that provides a user with the ability to monitor the current temperature and humidity of the object being observed, and a computer readable medium of the receiving device. The computer readable medium is used for storing code representing instructions that when executed at a processor cause the processor to store instructions to analyze values of temperature and humidity under the garment of the object and in the environment, received from the sensors of the at least one internal electronic module and the at least one external module to perform actions in order to personalize temperature and humidity control. Such actions include input of current values of temperature and humidity of the environment in manual mode, dividing all possible values of temperature and humidity into more than two zones, for example, comfort zone, border zone, critical zone input and adjustment of bounds on temperature and humidity zones, entering a time interval for a short-term forecast such as advance or early warning of the observer when critical temperatures are reached processes and outputs data on the values of temperature and humidity under the garment of the object and of the environment in the form of calculation of the rate of change of temperature and humidity, calculation of the time to reach critical temperatures, display of a graphic, text, and sound message on the receiving device with the current values of the temperature and humidity zones of the environment and the observed object, the rate of change of temperature and humidity of the environment and the observed object, the observed object's reaching the temperature and humidity values close to critical boundary, the observed object's reaching critical temperature and humidity values, a short-term forecast of reaching critical values of temperature and humidity, transmission of all information during an on-line monitoring session and its storage on a local server.

The external electronic module can be located on the clothes of the observed object. The at least one external electronic module is located at distance from the garment of the object, for example, on the clothes of the observer, on the bag, or on the stroller. The at least one internal electronic module and the at least one external electronic module includes a clip for fastening. The receiving device of the computer implemented system transmits the temperature and humidity values wirelessly (over the Internet) with the possibility to record the data to the local (remote) server (s). The computer readable medium storing code representing instructions that when executed at a processor cause the processor to store instructions to monitor temperature and humidity under a garment of an object to be observed, the computer readable medium executing an algorithm stored in a memory of a mobile computing device, comprising analyzing values of temperature and humidity under the garment of the object and in the environment, received from sensors of at least one internal electronic module and at least one external module to perform actions in order to personalize temperature and humidity control.

Wherein such actions include input of current values of temperature and humidity of the environment in manual mode, dividing all possible values of temperature and humidity into more than two zones, for example, comfort zone, border zone, critical zone input and adjustment of bounds on temperature and humidity zones, entering a time interval for a short-term forecast such as advance or early warning of the observer when critical temperatures are reached processes and outputs data on the values of temperature and humidity under the garment of the object and of the environment in the form of calculation of the rate of change of temperature and humidity.

The computer readable medium executing the algorithm stored in the memory of the mobile computing device also calculates the time to reach critical temperatures, display of a graphic, text, and sound message on the receiving device with the current values of the temperature and humidity zones of the environment and the observed object, the rate of change of temperature and humidity of the environment and the observed object, the observed object's reaching the temperature and humidity values close to critical boundary, the observed object's reaching critical temperature and humidity values, a short-term forecast of reaching critical values of temperature and humidity, followed by transmitting of all information during an on-line monitoring session and its storage on a local server.

An advantage of the present invention is to provide the inventive system for temperature and humidity monitoring under garment allows you to simplify the process of monitoring critical parameters of the state of the observed object, which in its turn allows you to take advance actions to prevent possible diseases that may be caused by going beyond specific, individual for each person, parameters.

Another advantage of the present invention is to provide the proposed system for monitoring temperature and humidity under clothing allows to simultaneously monitor the status of several objects.

The objects and advantages of the present invention will be more readily apparent from inspection of the following specification, taken in connection with the accompanying drawing, wherein like numerals refer to like parts throughout and in which an embodiment of the present invention is described and illustrated.

The exact manner in which the foregoing and other objects and advantages of the invention are achieved in practice will become more clearly apparent when reference is made to the following detailed description of the preferred embodiments of the invention described in detail in the following specification and shown in the accompanying drawings, where in like reference numbers indicate corresponding parts throughout.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
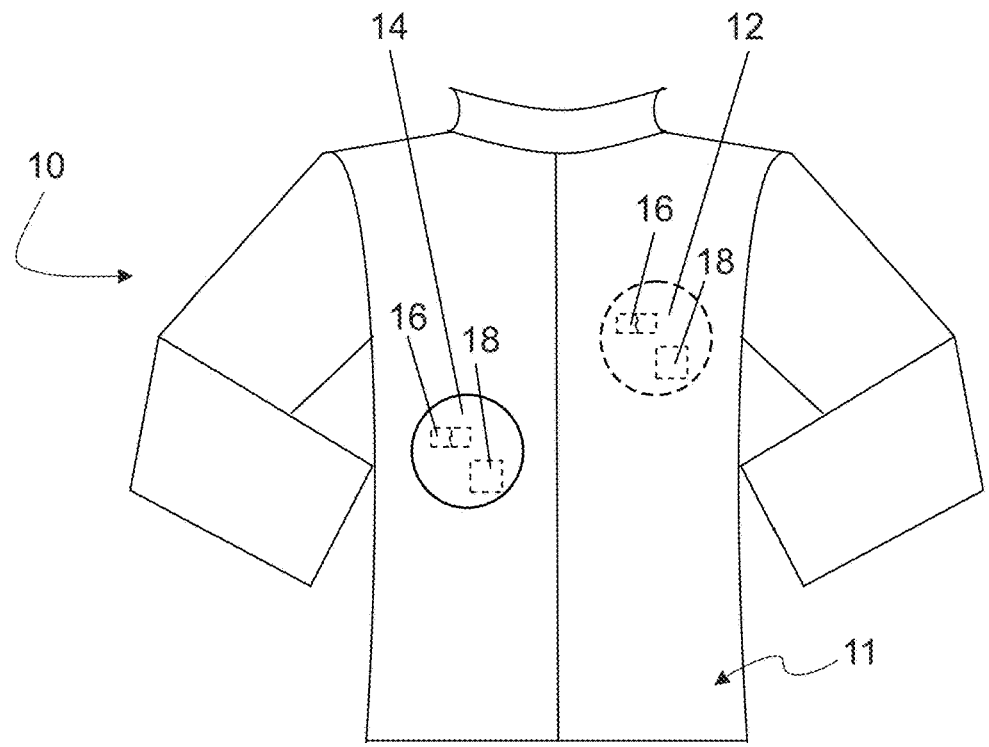
FIG. 1 illustrates a system for monitoring temperature and humidity under the garment.

Referring to the Figures, a system for monitoring temperature and humidity under the garment is generally shown at 10. Because explicit identification of object-oriented constructs expressed through the syntax of high-level object-oriented programming languages is lost during compilation to binary code (e.g., translation of a source code definition or representation of an application to a binary code definition or representation of the application such as a machine code or byte-code definition), potential security vulnerabilities can be obscured during static analysis of the resulting binary code.

For example, because information about an object (e.g., the class on which the object is based, the size of the object, the number and types or sizes of properties of the object, and the number of functionalities accessible to the object via a dispatch table) is typically not expressed in binary code, determining whether indirect operations relative to the object expose security vulnerabilities can be difficult without the source code from which the binary code was generated.

As a specific example, an indirect operation can result in arbitrary code execution security vulnerabilities if the binary code does not include run-time validation to ensure that the indirect operation does not operate outside or beyond the object (i.e., at memory addresses not allocated to or shared by the object). Some binary code representations of applications, however, do include information about objects. Such information can be included in binary code as run-time type information (RTTI) or debugging information that is compiled into the binary code. Nevertheless, because the binary code representations of many applications do not include such information (e.g., to discourage reverse engineering of these applications), robust methodologies and systems for analyzing binary code based on (or derived from) source code using object-oriented techniques should not assume availability of such information.

Implementations discussed herein analyze operations described in binary code to identify objects based on those operations. Said differently, implementations discussed herein reconstruct, at least partially, objects (or representations of objects) by inferring the structure of such objects based on operations described in binary code. Thus, implementations discussed herein can identify objects and attributes such as a size thereof without referring to (or independent of) source code or explicit information about such objects which may or may not be included in the binary code.

Furthermore, implementations discussed herein perform security vulnerability analyses of binary code representations of applications using such objects. For example, implementations discussed herein can identify security vulnerabilities such as type confusion vulnerabilities that can result in arbitrary code execution, code injection, application failure, or other undesirable or unintended behavior of an application using information about objects identified by analysis of operations described in binary code.

Accordingly, implementations discussed herein with reference to analysis of operations described in binary code should be understood to refer to analysis of those operations using a binary code representation of a software module or a representation of the software module derived from the binary code representation.

A variable within a memory is a memory location at which one or more values can be stored. Such a memory location can be at a processor memory (e.g., a register or cache), at a system memory (e.g., a Random Access Memory (RAM) of a computing system), or at some other memory. Operations within binary code that operate on such variables can refer to a memory address (either absolute or relative to another memory address such as an offset from a stack pointer) of that memory location. Thus, the identifier (e.g., memory address) of an object can be stored as a value at a memory location with a memory address that is used by operations within the binary code.

Accordingly, as used herein, terms such as "identifier of an object" and "memory address of an object" should be understood to refer to the identifier (e.g., memory address) itself or to a variable at which a value representing the identifier is stored. As used herein, the term "module" refers to a combination of hardware (e.g., a processor such as an integrated circuit or other circuitry) and software (e.g., machine- or processor-executable instructions, commands, or code such as firmware, programming, or object code).

A combination of hardware and software includes hardware only (i.e., a hardware element with no software elements), software hosted at hardware (e.g., software that is stored at a memory and executed or interpreted at a processor), or at hardware and software hosted at hardware.

Additionally, as used herein, the singular forms "a," "an," and "the" include plural referents unless the context clearly dictates otherwise. Thus, for example, the term "module" is intended to mean one or more modules or a combination of modules. Furthermore, as used herein, the term "based on" includes based at least in part on. Thus, a feature that is described as based on some cause, can be based only on that cause, or based on that cause and on one or more other causes.

It will be apparent that multiple embodiments of this disclosure may be practiced without some or all of these specific details. In other instances, well-known process operations have not been described in detail in order not to unnecessarily obscure the present embodiments. The following description of embodiments includes references to the accompanying drawing. The drawing shows illustrations in accordance with example embodiments. These example embodiments, which are also referred to herein as "examples," are described in enough detail to enable those skilled in the art to practice the present subject matter. The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

Alluding to the above, for purposes of this patent document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprising," "include," and "including" are interchangeable and not intended to be limiting. For example, the term "including" shall be interpreted to mean "including, but not limited to."

The system 10 is designed to monitor individual body temperature and to manage alarms and access in areas with flows of people in transit such as hospitals, supermarkets, railway stations, schools, airports, companies, offices, shopping centers, and the like. The problem is solved by the proposed system for monitoring temperature and humidity under the clothing, which, according to the invention, contains at least one internal electronic module located under the garment, and an external electronic module with temperature and humidity sensors and internal storage device, connected to the electronic modules wirelessly (via Bluetooth), a receiving device that monitors current temperature and humidity values of the observed object.

The presence of at least one internal electronic module located under the garment, and an external electronic module with temperature and humidity sensors, provides the ability to simultaneously monitor two vital parameters of a person's condition, and the presence of the internal storage device in electronic modules provides data recording in case of a radio communication failure; connected to the electronic modules via wireless communication, the receiving device provides the ability to visually monitor the observed object for current temperature and humidity values. As a wireless connection type, a Bluetooth can be used.

Using a receiving device with wireless communication makes it possible to position an external electronic module not only on the garment of the observed object, but also far from the observed object, for example, on a garment of the observer, on a bag or on a stroller. Using a smartphone as a receiving device provides the ability to transmit temperature and humidity values wirelessly on-line (over the Internet) with the ability to record this data to a remote server (s). The presence of clips provides a convenient and reliable fastening of electronic modules.

Thus, the claimed invention allows to simplify the process of monitoring critical parameters of the state of the observed object under the garment, which in turn allows you to take advance action to prevent possible diseases that may be caused by going beyond specific and individual for each person parameters.

Figure 2:
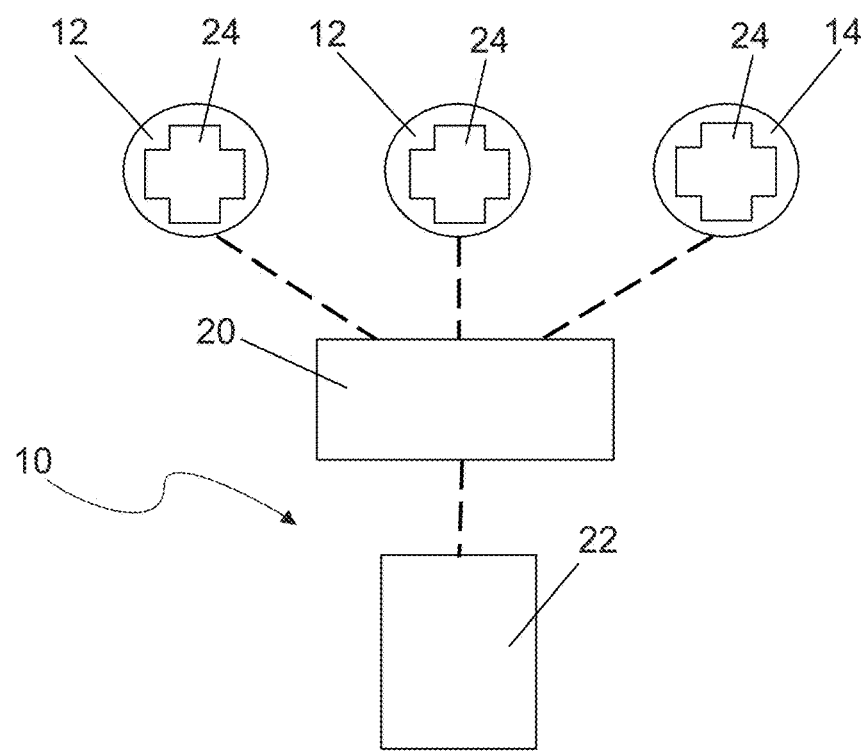
FIG. 2 illustrates a functional diagram of the system for temperature and humidity monitoring under the garment.

Referring now to FIGS. 1 and 2, the system 10 for monitoring temperature and humidity under the garment 11 includes at least one internal electronic module 12 located under the garment 11, at least one external electronic module 14 with temperature and humidity sensors 16 for measuring temperature and humidity under the garment and for measuring temperature and humidity of the environment, and at least one internal storage device 18, and a receiver 20 connected to electronic modules 12 and 14 via Bluetooth.

The receiving device 20, such as a smartphone, is equipped with light and sound indicators, providing the ability to visually monitor the current values of temperature and humidity. The receiving device 20 transmits the temperature and humidity values wirelessly on-line (over the Internet) with the ability to record this data to at least remote server (s) 22.

Using the smartphone as the receiving device 20 allows to optimize the number of system elements due to the fact that data received from temperature and humidity sensors, as well as visual control of temperature and humidity, sound notification of reaching critical temperature and humidity values and remote control arc all carried out by one device.

The quantity of the internal modules 12 can be more than one, and they can be located at different places under the garment of one observed object, for example, on the arm, on the foot, on the back. In addition, the internal modules 1 can be located under the garments of several observed objects, which allows the use of the inventive system for simultaneous monitoring of several objects. The electronic modules 12 and 14 are equipped with a clip 24, which provides a convenient and reliable fastening under the garment, on top of the garment or to any object with an external surface located in a convenient place for the observed object or observer.

The inventive system for temperature and humidity monitoring under garment works as follows. The internal electronic module 12 with the sensors 16 and the internal storage device 18 is fixed with the help of the clip 24 under the garments 11 of one or more of the observed objects for temperature and humidity measuring. The external electronic module 14 with the sensors 16 and the internal storage device 18 is fixed with the help of the clip 24 to the outerwear 11, for example, a jacket or pram, for measuring the temperature and humidity of the environment. The temperature and humidity values from the external and internal modules 12 and 14 are transmitted via wireless communication, for example, via Bluetooth radio channel, to the receiving device 20 (smartphone) located in the inner pocket or in another place convenient for the observer.

The presence in the electronic modules 12 and 14 of the internal storage device 18 provides an opportunity to record temperature and humidity values in the event of a failure of wireless communication with the receiving device 20. The receiving device 20 displays the current values of temperature and humidity, gives sound and/or light signals notifying the user when the temperature or humidity under the garment or of the environment reaches critical values.

The receiving device 20 provides remote control: it transmits the temperature and humidity values to third parties wirelessly on-line (over the Internet) for recording the data to the local (remote) server (s) 22. To analyze the values of temperature and humidity under the garment of the observed object and in the environment, received from the sensors 16 of the internal and external modules 12 and 14, a software is installed on the receiving device 20 (smartphone) with the ability to perform the following actions in order to personalize temperature and humidity control: input of current values of temperature and humidity of the environment (in manual mode/from weather forecast sites via the Internet); dividing all possible values of temperature and humidity into more than two zones, for example, comfort zone, border zone, critical zone; input/adjustment of bounds on temperature and humidity zones; entering a time interval for a short-term forecast—advance or early warning of the observer when critical temperatures are reached.

In addition, the installed software processes and outputs data on the values of temperature and humidity under the garment of the object and of the environment in the form of: calculation of the rate of change of temperature and humidity; calculation of the time to reach critical temperatures;

display of a graphic/text/sound message on the receiving device 5 with the current values of the temperature and humidity zones of the environment and the observed object; the rate of change of temperature and humidity of the environment and the observed object; the observed object's reaching the temperature and/or humidity values close to critical (boundary); the observed object's reaching critical temperature and/or humidity values; a short-term forecast of reaching critical values of temperature and humidity; transmission of all information during an on-line monitoring session and its storage on a local (remote) server.

Thus, the inventive system 10 for temperature and humidity monitoring under garment allows you to simplify the process of monitoring critical parameters of the state of the observed object, which in its turn allows you to take advance actions to prevent possible diseases that may be caused by going beyond specific, individual for each person, parameters. In addition, the proposed system for monitoring temperature and humidity under clothing allows you to simultaneously monitor the status of several objects.

Figure 3A:
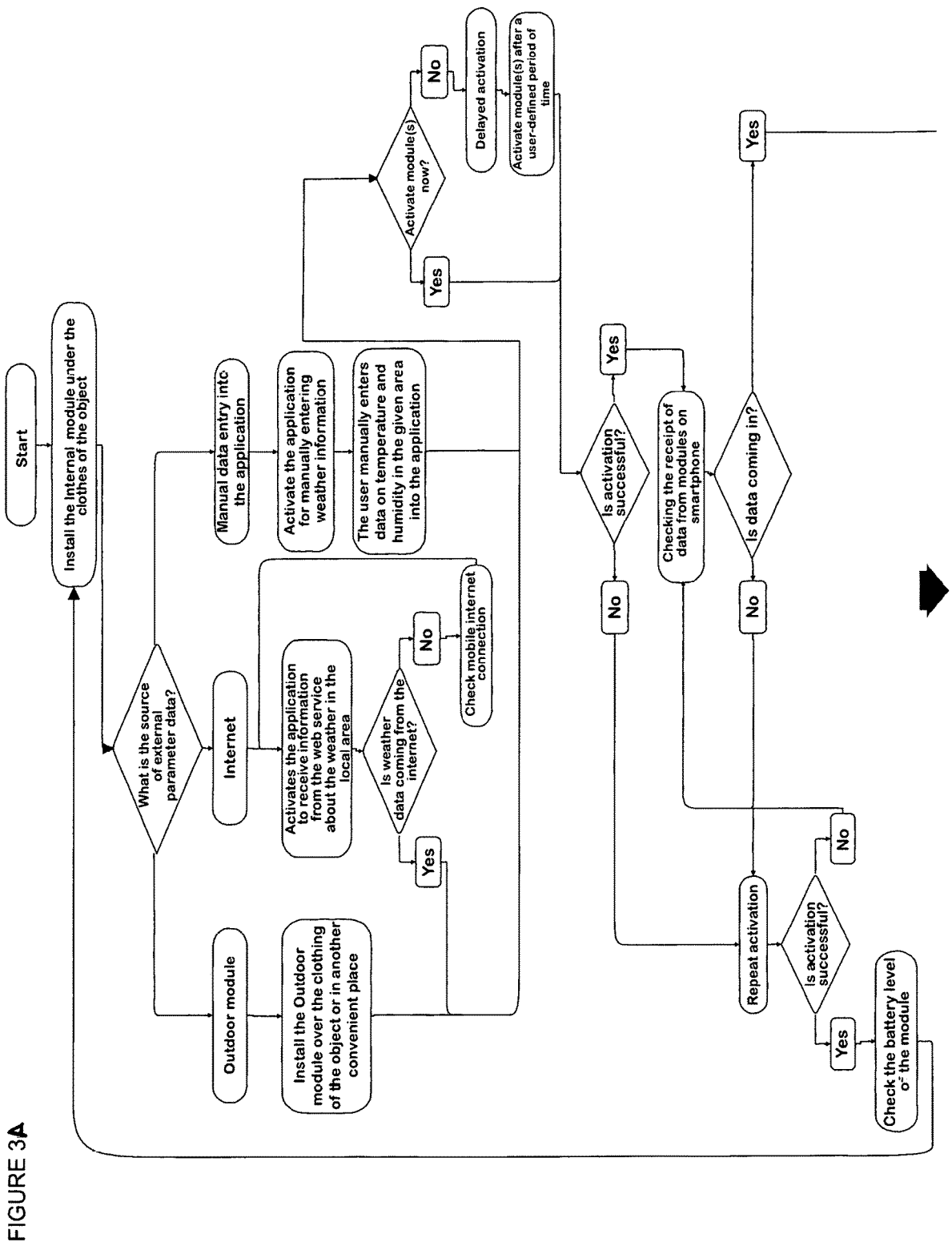
FIGS. 3A through 3C illustrate a first part of a functional diagram of an algorithm of the system for temperature and humidity monitoring under the garment.
Figure 3B:
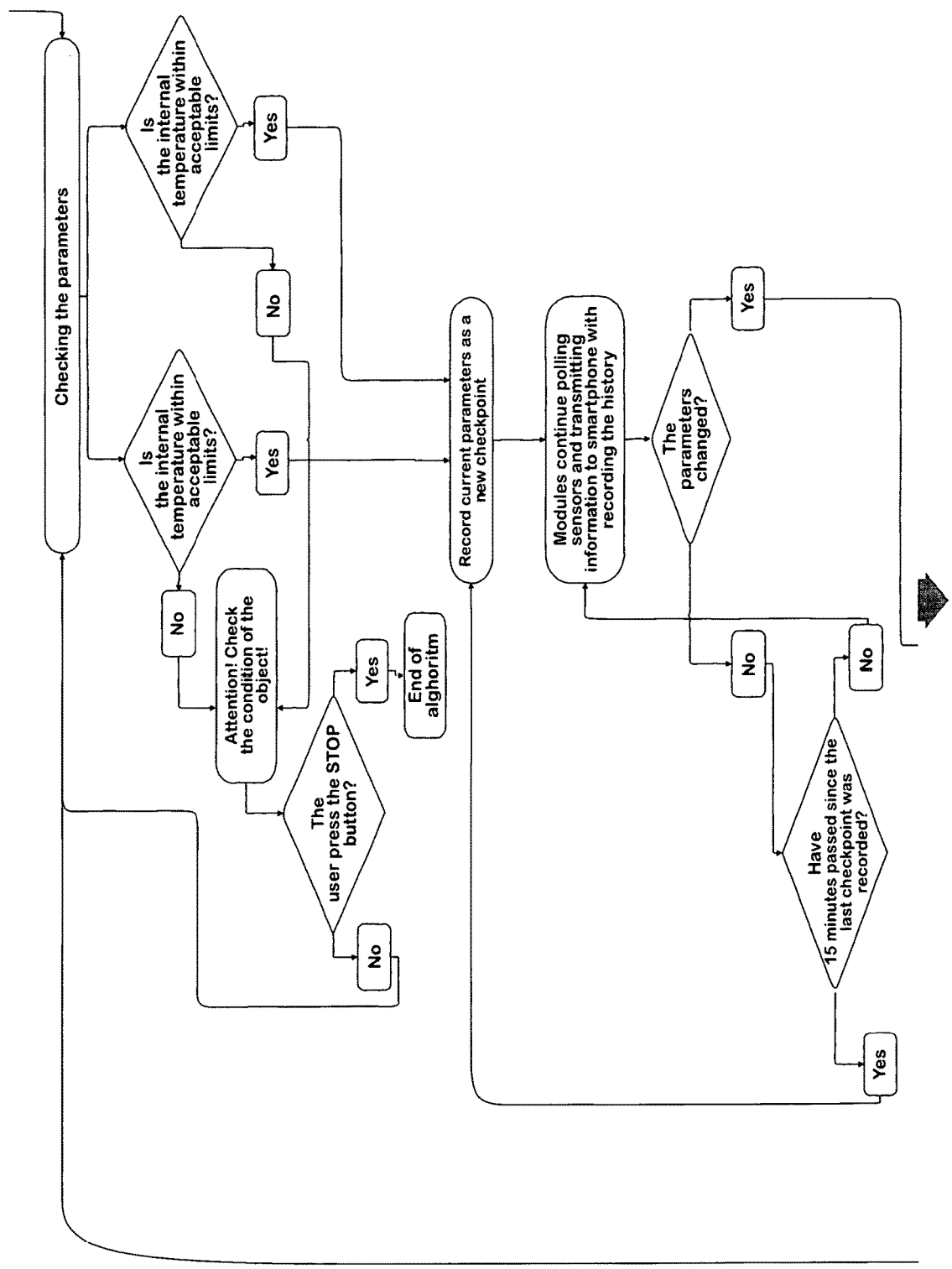
Figure 3C:
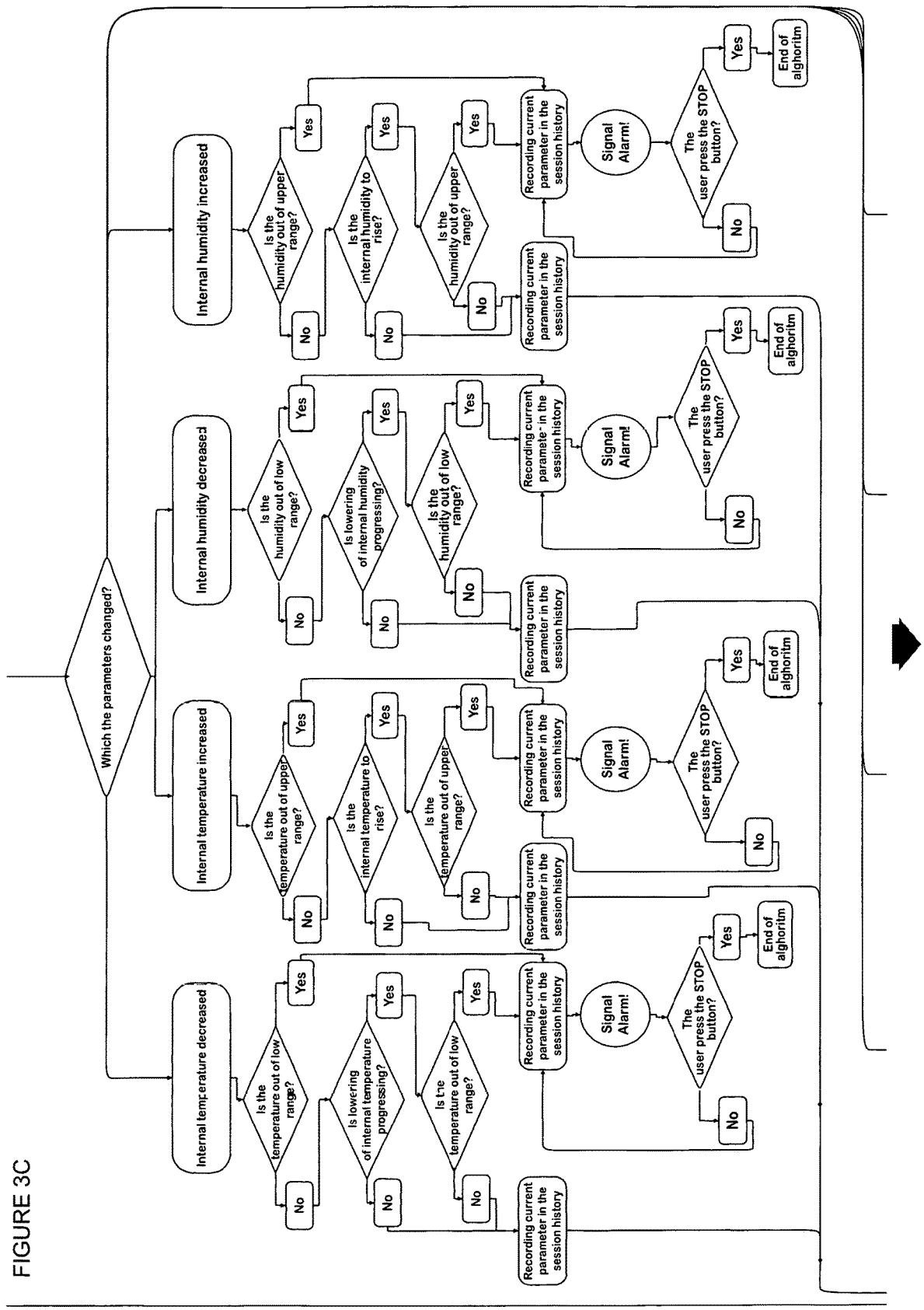
Figure 4A:
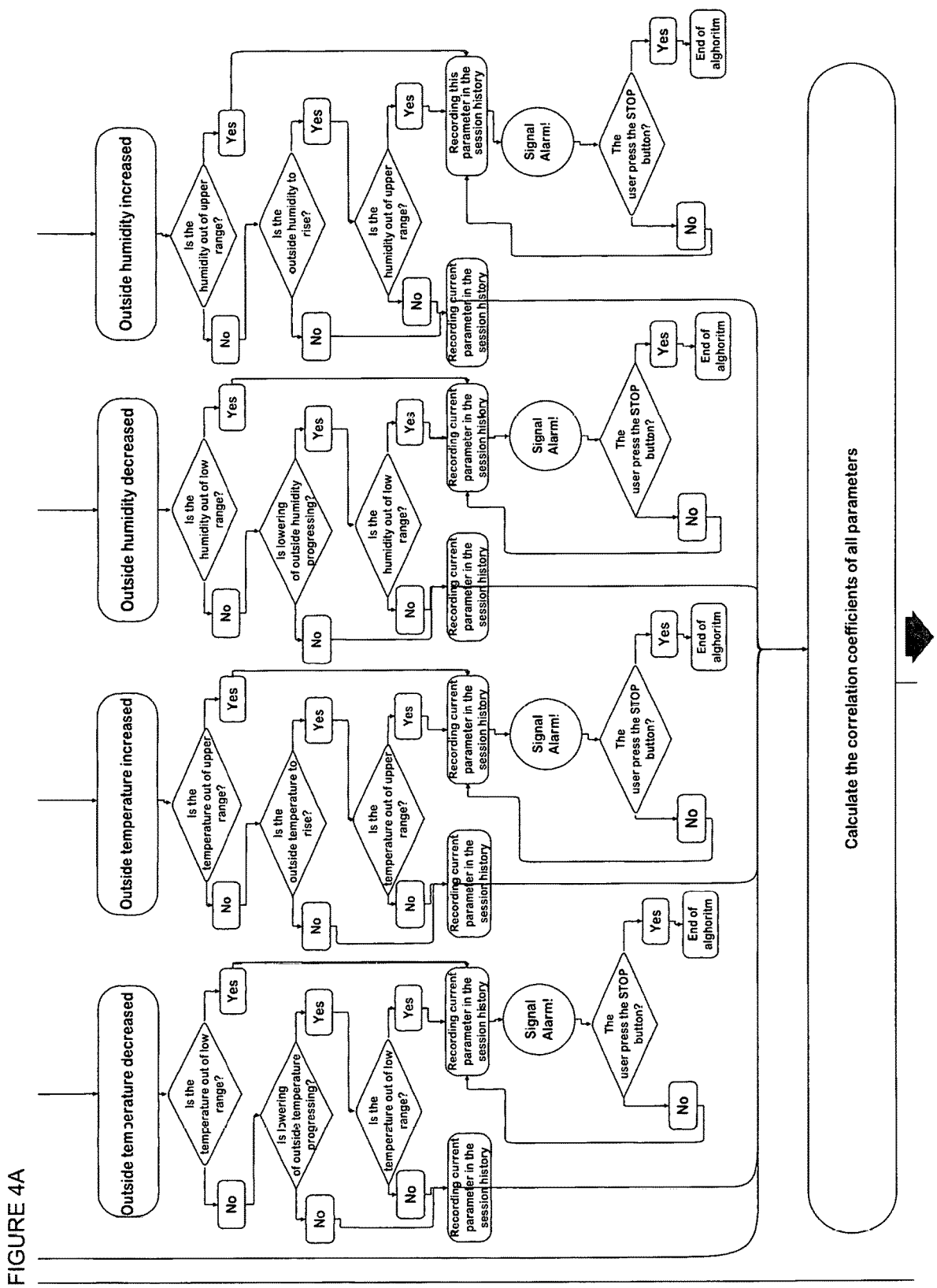
FIGS. 4A through 4B illustrate a second part of the functional diagram of the algorithm of the system, as shown in FIGS. 3A through 3C, for temperature and humidity monitoring under the garment.
Figure 4B:
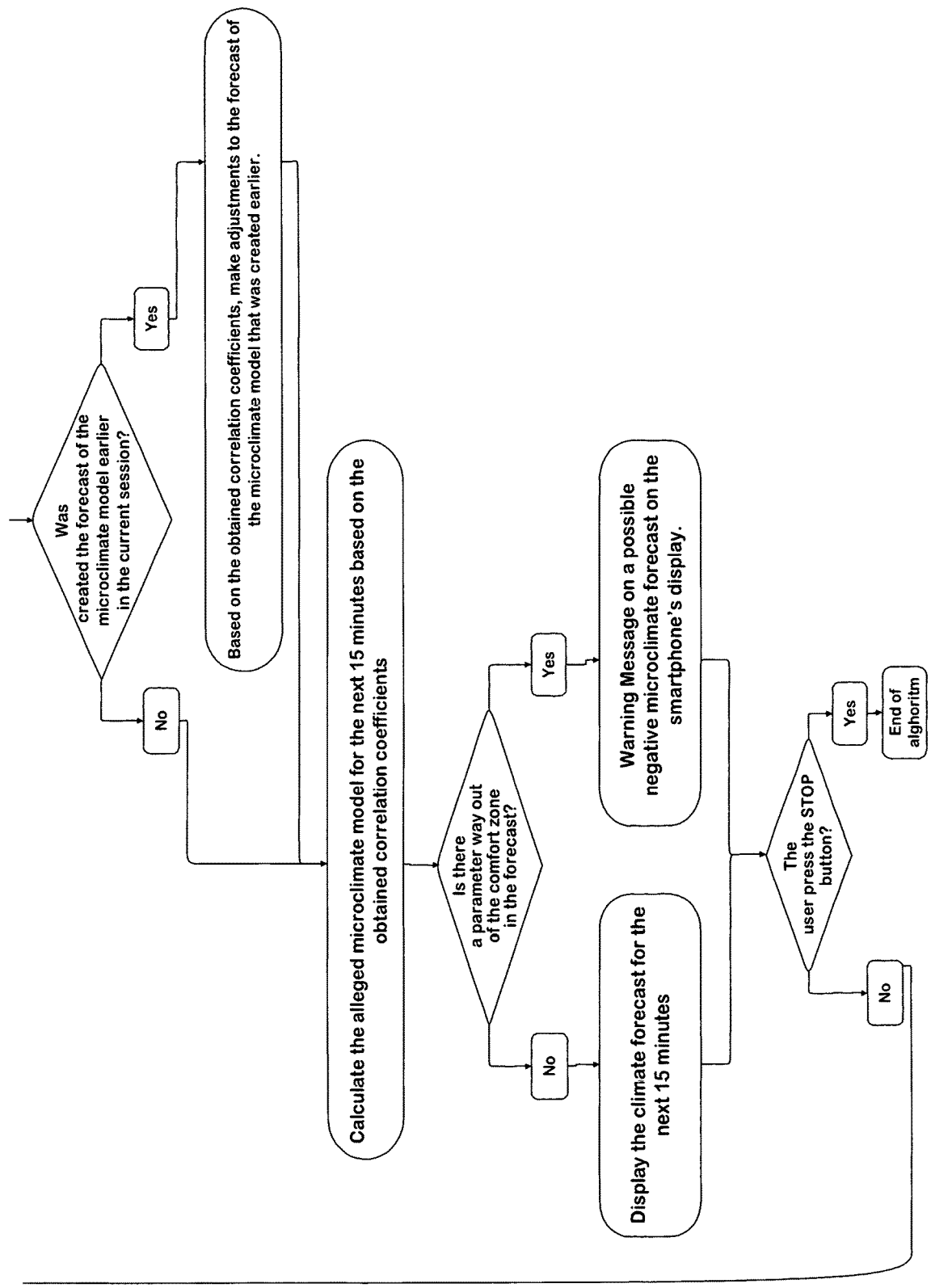

Referring to FIGS. 3 and 4, these figures illustrate a functional diagram of an algorithm of the system for temperature and humidity monitoring under the garment. Algorithm starts 100 with the installation the internal module under the clothes of the object 102. Then, depending on the source of external parameter data 104 the following steps are taken. If the source of external parameter data is outdoor module 106, than the algorithm decides to install the outdoor module over the clothing of the object or in another convenient place 112. After that the algorithm decides whether to activate module(s) now 124.

In another case if external parameter data is download from Internet 108 the algorithm activates the application to receive information from the web service about the weather in the local area 114. Than if weather data is not coming from the internet 118 algorithm checks mobile internet connection 122. And In this case, the algorithm returns us to the command 114. If data is coming from the internet than the algorithm decides whether to activate module(s) now 124. However if the source of external parameter data is manual data, which is entered into the application 110, than it proceeds to activate the application for manually entering weather information 116 and the user could manually enter data on temperature and humidity in the given area into the application 120. After that the algorithm decides whether to activate module(s) now 124.

If the algorithm decides to activate the module (s) 124 it checks whether the activation is successful 130. However, the algorithm may decides not to activate the module (s) now 124, so delayed activation may be established 126 based on a user-defined period of time 128. After algorithm checks whether the activation is successful 130. If activation passed successfully algorithm proceeds with checking the receipt of data from modules on smartphone 132 and then it is determined whether data coming in 136. Otherwise the system provides repeat activation 134 and decides whether it is successful or not 138.

If repeat activation is successful 138 algorithm proceeds with checking the receipt of data from modules on smartphone 132 and then it is determined whether data coming in 136. However, if repeat activation 134 is not successful the algorithm checks the battery level of the module 140 and then repeats the sequence of steps from step "install the internal module under the clothes of the object" 102. Then if it is determined that the data is coming in 136 correctly system starts checking the parameters 142.

However, if the algorithm determines that the data is not coming in, it proceeds with repeat activation 134 of the system and decides whether it is successful or not 138. If repeat activation is successful algorithm repeatedly proceeds with checking the receipt of data from modules on smartphone 132 and then it is determined whether data coming in 136. However If repeat activation is not successful the algorithm checks the battery level of the module 140 and than repeats the sequence of steps from step "install the internal module under the clothes of the object" 102 unless the following sequence of steps will not succeed data coming within the step 136.

While checking the parameters 142 the system defines in parallel first is the internal temperature within acceptable limits? 144 and the second is the internal humidity within acceptable limits? 146 If the internal temperature is within acceptable limits the algorithm provides with the record current parameters as a new checkpoint 154. If the index of internal temperature is not within acceptable limits the algorithm displays a message "Attention! Check the condition of the object!" 148, so the user then can press the "STOP" button 150.

Therefore, if the user does so, it means the end of algorithm execution 152, if no—the algorithm returns to checking the parameters 142 and performs the following steps again. If the internal humidity is within acceptable limits the algorithm provides with the record current parameters as a new checkpoint 154. If the index of internal humidity is not within acceptable limits the algorithm displays a message "Attention! Check the condition of the object!" 148, so the user then can press the "STOP" button 150. Therefore, if the user does so, it means the end of algorithm execution 152, if no—the algorithm returns to checking the parameters 142 and performs the following steps again.

After algorithm records current parameters as a new checkpoint 154, modules of the system continue polling sensors and transmitting information to smartphone with recording the history 156. Then algorithm decides whether the parameters changed 158. If the parameters changed the system goes on to determine which the parameters changed 162. If the algorithm establishes that no parameters changed it after that decides whether 15 minutes passed since the last checkpoint was recorded 160, if this time passed the algorithm returns to the step of recording current parameters as a new checkpoint 154 and performs the following steps repeatedly. If 15 minutes has not passed since the last checkpoint was recorded 160, the modules continue polling sensors and transmitting information to smartphone with recording the history 156 and then algorithm proceeds to exercise the following steps.

While defining which the parameters changed 162 system firstly establishes whether internal temperature decreased 164; for that reason, algorithm decides whether the temperature is out of low range 172. If the temperature is out of low range, it exercises the command "recording current parameter in the session history" 198. After that the system displays signal "Alarm!" 212, so the user then can press the "STOP" button 220. Therefore, if the user does so, it means the end of algorithm execution 228, if no—the algorithm returns to exercise the command "recording current parameter in the session history" 198 and then proceeds the execution of the following steps.

If the temperature is not out of low range, the algorithm decides whether lowering of internal temperature progressing 180. If lowering of internal temperature is progressing, the algorithm than decides repeatedly is the temperature out of low range 188. If the temperature is out of low range, it exercises the command "recording current parameter in the session history" 196. After that the system displays signal "Alarm!" 212, so the user then can press the "STOP" button 220. Therefore, if the user do so, it means the end of algorithm execution 228, if no—the algorithm returns to exercise the command "recording current parameter in the session history" 198 and then proceeds the execution of the following steps.

If during reevaluation process of temperature's range the algorithm decides the temperature is not out of low range 188, the system exercises the command "recording current parameter in the session history" 196 for future execution of calculation the correlation coefficients of all parameters 308. If lowering of internal temperature is not progressing 180, the system exercises the command "recording current parameter in the session history" 196 for future execution of calculation the correlation coefficients of all parameters 308.

While defining which the parameters changed 162 system secondly establishes whether internal temperature increased 166; for that reason, algorithm decides whether the temperature is out of upper range 174. If the temperature is out of upper range, it exercises the command "recording current parameter in the session history" 202. After that the system displays signal "Alarm!" 214, so the user then can press the "STOP" button 222. Therefore, if the user does so, it means the end of algorithm execution 230, if no—the algorithm returns to exercise the command "recording current parameter in the session history" 202 and then proceeds the execution of the following steps.

If the temperature is not out of upper range 174, the algorithm decides whether internal temperature is to rise 182. If internal temperature is to rise, the algorithm than decides repeatedly is the temperature out of upper range 190. If the temperature is out of upper range, it exercises the command "recording current parameter in the session history" 202. After that the system displays signal "Alarm!" 214, so the user then can press the "STOP" button 222. Therefore, if the user do so, it means the end of algorithm execution 230, if no—the algorithm returns to exercise the command "recording current parameter in the session history" 202 and then proceeds the execution of the following steps. If during reevaluation process of temperature's range the algorithm decides the temperature is not out of upper range 190, the system exercises the command "recording current parameter in the session history" 200 for future execution of calculation the correlation coefficients of all parameters 308. If 1 internal temperature is not to rise 182, the system exercises the command "recording current parameter in the session history" 200 for future execution of calculation the correlation coefficients of all parameters 308.

While defining which the parameters changed 162 system establishes thirdly whether internal humidity decreased 168; for that reason, algorithm decides whether the humidity is out of low range 176. If the humidity is out of low range, it exercises the command "recording current parameter in the session history" 206. After that the system displays signal "Alarm!" 216, so the user then can press the "STOP" button 224. Therefore, if the user does so, it means the end of algorithm execution 232, if no—the algorithm returns to exercise the command "recording current parameter in the session history" 206 and then proceeds the execution of the following steps.

If the humidity is not out of low range 176, the algorithm decides whether lowering of internal humidity progressing 184. If lowering of internal humidity is progressing, the algorithm than decides repeatedly is the humidity out of low range 192. If the humidity is out of low range, it exercises the command "recording current parameter in the session history" 206. After that the system displays signal "Alarm!" 216, so the user then can press the "STOP" button 224. Therefore if the user do so, it means the end of algorithm execution 232, if no—the algorithm returns to exercise the command "recording current parameter in the session history" 206 and then proceeds the execution of the following steps.

If during reevaluation process of humidity's range the algorithm decides the humidity is not out of low range 192, the system exercises the command "recording current parameter in the session history" 204 for future execution of calculation the correlation coefficients of all parameters 308. If lowering of internal humidity is not progressing 184, the system exercises the command "recording current parameter in the session history" 204 for future execution of calculation the correlation coefficients of all parameters 308.

While defining which the parameters changed 162 system in-fourth establishes whether internal humidity increased 170; for that reason, algorithm decides whether the humidity is out of upper range 178. If the humidity is out of upper range, it exercises the command "recording current parameter in the session history" 210. After that the system displays signal "Alarm!" 218, so the user then can press the "STOP" button 226. Therefore if the user does so, it means the end of algorithm execution 234, if no—the algorithm returns to exercise the command "recording current parameter in the session history" 210 and then proceeds the execution of the following steps.

If the humidity is not out of upper range 178, the algorithm decides whether internal humidity is to rise 186. If internal humidity is to rise, the algorithm than decides repeatedly is the humidity out of upper range 194. If the humidity is out of upper range, it exercises the command "recording current parameter in the session history" 210. After that the system displays signal "Alarm!" 218, so the user then can press the "STOP" button 226.

Therefore if the user do so, it means the end of algorithm execution 234, if no—the algorithm returns to exercise the command "recording current parameter in the session history" 210 and then proceeds the execution of the following steps. If during reevaluation process of humidity's range the algorithm decides the humidity is not out of upper range 194, the system exercises the command "recording current parameter in the session history" 208 for future execution of calculation the correlation coefficients of all parameters 308. If 1 internal humidity is not to rise 186, the system exercises the command "recording current parameter in the session history" 208 for future execution of calculation the correlation coefficients of all parameters 308.

While defining which the parameters changed 162 system fifthly establishes whether outside temperature decreased 236; for that reason algorithm decides whether the temperature is out of low range 244. If the temperature is out of low range, it exercises the command "recording current parameter in the session history" 270. After that the system displays signal "Alarm!" 281, so the user then can press the "STOP" button 292. Therefore if the user does so, it means the end of algorithm execution 300, if no—the algorithm returns to exercise the command "recording current parameter in the session history" 270 and then proceeds the execution of the following steps.

If the temperature is not out of low range 244, the algorithm than decides whether lowering of outside temperature progressing 252. If lowering of outside temperature is progressing, the algorithm than decides repeatedly is the temperature out of low range 260. If the temperature is out of low range, it exercises the command "recording current parameter in the session history" 270.

After that the system displays signal "Alarm!" 284, so the user then can press the "STOP" button 292. Therefore if the user do so, it means the end of algorithm execution 300, if no—the algorithm returns to exercise the command "recording current parameter in the session history" 270 and then proceeds the execution of the following steps. If during reevaluation process of temperature's range the algorithm decides the temperature is not out of low range 260, the system exercises the command "recording current parameter in the session history" 268 for future execution of calculation the correlation coefficients of all parameters 308. If lowering of internal temperature is not progressing 244, the system exercises the command "recording current parameter in the session history" 268 for future execution of calculation the correlation coefficients of all parameters 308.

While defining which the parameters changed 162 system establishes at sixth whether outside temperature increased 238; for that reason algorithm decides whether the temperature is out of upper range 246. If the temperature is out of upper range, it exercises the command "recording current parameter in the session history" 282. After that the system displays signal "Alarm!" 286, so the user then can press the "STOP" button 294. Therefore if the user does so, it means the end of algorithm execution 302, if no—the algorithm returns to exercise the command "recording current parameter in the session history" 282 and then proceeds the execution of the following steps.

If the temperature is not out of upper range 246, the algorithm decides whether outside temperature is to rise 254. If outside temperature is to rise, the algorithm than decides repeatedly is the temperature out of upper range 262. If the temperature is out of upper range, it exercise the command "recording current parameter in the session history" 282 After that the system displays signal "Alarm!" 286, so the user then can press the "STOP" button 294.

Therefore if the user do so, it means the end of algorithm execution 302, if no—the algorithm returns to exercise the command "recording current parameter in the session history" 282 and then proceeds the execution of the following steps. If during reevaluation process of temperature's range the algorithm decides the temperature is not out of upper range 262, the system exercises the command "recording current parameter in the session history" 272 for future execution of calculation the correlation coefficients of all parameters 308. If 1 internal temperature is not to rise 254, the system exercises the command "recording current parameter in the session history" 272 for future execution of calculation the correlation coefficients of all parameters 308.

While defining which the parameters changed 162 system establishes in the seventh whether outside humidity decreased 240; for that reason, algorithm decides whether the humidity is out of low range 248. If the humidity is out of low range, it exercises the command "recording current parameter in the session history" 278. After that the system displays signal "Alarm!" 288 so the user then can press the "STOP" button 296. Therefore if the user does so, it means the end of algorithm execution 304, if no—the algorithm returns to exercise the command "recording current parameter in the session history" 278 and then proceeds the execution of the following steps.

If the humidity is not out of low range 248, the algorithm decides whether lowering of outside humidity progressing 256. If lowering of outside humidity is progressing 256, the algorithm than decides repeatedly is the humidity out of low range 264. If the humidity is out of low range, it exercises the command "recording current parameter in the session history" 278. After that the system displays signal "Alarm!" 288, so the user then can press the "STOP" button 296.

Therefore if the user do so, it means the end of algorithm execution 304, if no—the algorithm returns to exercise the command "recording current parameter in the session history" 278 and then proceeds the execution of the following steps. If during reevaluation process of humidity's range the algorithm decides the humidity is not out of low range 264, the system exercises the command "recording current parameter in the session history" 276 for future execution of calculation the correlation coefficients of all parameters 308. If lowering of internal humidity is not progressing 248, the system exercises the command "recording current parameter in the session history" 276 for future execution of calculation the correlation coefficients of all parameters 308.

While defining which the parameters changed 162 system in the eighth establishes whether outside humidity increased 242; for that reason algorithm decides whether the humidity is out of upper range 250. If the humidity is out of upper range, it exercises the command "recording current parameter in the session history" 282. After that the system displays signal "Alarm!" 290, so the user then can press the "STOP" button 298. Therefore if the user does so, it means the end of algorithm execution 306, if no—the algorithm returns to exercise the command "recording current parameter in the session history" 282 and then proceeds the execution of the following steps.

If the humidity is not out of upper range 250, the algorithm decides whether outside humidity is to rise 258. If outside humidity is to rise, the algorithm than decides repeatedly is the humidity out of upper range 266. If the humidity is out of upper range, it exercises the command "recording current parameter in the session history" 282. After that the system displays signal "Alarm!" 290, so the user then can press the "STOP" button 298. Therefore if the user do so, it means the end of algorithm execution 306, if no—the algorithm returns to exercise the command "recording current parameter in the session history" 282 and then proceeds the execution of the following steps.

If during reevaluation process of humidity's range the algorithm decides the humidity is not out of upper range 266, the system exercises the command "recording current parameter in the session history" 280 for future execution of calculation the correlation coefficients of all parameters 308. If 1 internal humidity is not to rise 258, the system exercises the command "recording current parameter in the session history" 280 for future execution of calculation the correlation coefficients of all parameters 308.

After the algorithm has calculated the correlation coefficients of all parameters 308, it than defines whether the forecast of the microclimate model was created earlier in the current session 310. When the forecast of the microclimate model was created earlier in the current session the algorithm adjusts the forecast of the microclimate model that was created earlier based on the obtained correlation coefficients 312 and then starts to calculate the alleged microclimate model for the next 15 minutes based on the obtained correlation coefficients 314.

If the forecast of the microclimate model was not created earlier in the current session 310 the algorithm than starts to calculate the alleged microclimate model for the next 15 minutes based on the obtained correlation coefficients 314. After that the system decides whether there is a parameter way out of the comfort zone in the forecast 316. If a parameter way out of the comfort zone is present in the forecast, than the system initiates displaying of the warning message on a possible negative microclimate forecast on the smartphone's display 320; so the user then can press the "STOP" button 322.

Therefore, if the user does so, it means the end of algorithm execution 324, if no—the algorithm returns to exercise the command "checking the parameters" 142 and then proceeds the execution of the following steps. If a parameter way out of the comfort zone is not present in the forecast, the system initiates displaying the climate forecast for the next 15 minutes 318; so the user then can press the "STOP" button 322. Therefore, if the user does so, it means the end of algorithm execution 324, if no—the algorithm returns to exercise the command "checking the parameters" 142 and then proceeds the execution of the following steps.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A computer-implemented system for temperature and humidity monitoring under a garment of an object to be observed, said system comprising:
    at least one internal electronic module located internal to the garment and configured to measure temperature and humidity of the object;
    at least one external electronic module located external to the garment and configured to measure temperature and humidity of an outside environment, said at least one internal and external electronic modules each including at least one sensor for the temperature and humidity monitoring and each including an internal storage device; and
    a receiving device connected in wireless communication to said at least one internal and external electronic modules and configured to display to a user current temperature and humidity of the object being observed, said receiving device comprising a processor and a non-transitory computer-readable medium having non-transitory computer-readable program code stored thereon, wherein said processor is configured to execute the computer-readable program code to:
        measure and display values representing the temperature and humidity of the object and of the outside environment to the user or transmit the values to a third party;
        provide an analysis of the values representing the temperature and humidity of the object and of the outside environment to the user or third party; and
        prompt the user or third party to select a source of the values representing the temperature and humidity of the outside environment, the source is being selected from the group consisting of a manual input, an Internet download, and said external electronic module;
    wherein the analysis of the values representing the temperature and humidity of the object and of the outside environment includes (a) a calculation of a rate of change of the temperature and humidity of the object, (b) a calculation of time to reach a critical temperature or humidity, and (c) a forecast of reaching the critical temperature or humidity.

2. The computer-implemented system of claim 1, wherein said processor is further configured to identify to the user or third party more than two zones each representing parameters of the temperature and humidity for the object being observed.

3. The computer-implemented system of claim 2, wherein the zones include a comfort zone, a border zone, and a critical zone for the object being observed, and wherein the parameters of the temperature and humidity of each zone for the object are selectively adjustable by the user or third party.

4. The computer-implemented system of claim 1, wherein said processor is further configured to display or sound to the user or third party a graphical or sound alert based on the values representing the temperature and humidity of the object being observed.

5. The computer-implemented system of claim 1, wherein said processor is further configured to calculate a rate of change of the temperature and humidity of the outside environment.

6. The computer-implemented system of claim 1, wherein in response to said external electronic module being selected by the user or third party as the source of the values representing the temperature and humidity of the outside environment, the processor is configured to activate said external electronic module.

7. The computer-implemented system of claim 1, wherein in response to the Internet download being selected by the user or third party as the source of the values representing the temperature and humidity of the outside environment, the processor is configured to activate an application to receive temperature and humidity information from a weather web service.

* * * * *